United States Patent [19]

Vyas

[11] Patent Number: 5,017,558

[45] Date of Patent: * May 21, 1991

[54] SYNTHETIC VACCINE PEPTIDE EPITOMES OF HEPATITIS B SURFACE ANTIGEN

[75] Inventor: Girish N. Vyas, Orinda, Calif.

[73] Assignee: The Regents of the University of California, Oakland, Calif.

[ * ] Notice: The portion of the term of this patent subsequent to Nov. 15, 2000 has been disclaimed.

[21] Appl. No.: 532,231

[22] Filed: Sep. 13, 1983

Related U.S. Application Data

[63] Continuation of Ser. No. 112,054, Jan. 14, 1980, Pat. No. 4,415,491.

[51] Int. Cl.⁵ ............... A61K 37/00; A61K 37/02
[52] U.S. Cl. ..................... 514/14; 514/13; 514/12; 514/2; 424/88; 424/89; 530/324; 530/325; 530/326; 530/327; 530/826; 530/806; 530/807
[58] Field of Search ............ 424/85, 88, 89, 177, 424/89; 260/112.5 R; 514/2, 8, 12–14; 530/324–328, 826, 806, 807

[56] References Cited

PUBLICATIONS

Arnon, *Pharmac. Ther.;* vol. 6, 1979, pp. 275–289, "Anti--viral activity induced by synthetic peptides corresponding to regions involved in viral neutralization".

Rao et al., *Microbios,* vol. 10, 1974, "Structure and activity of hepatitis B antigen (HBAg) 2 Amino acid composition . . . ".

Bancroft et al., *J. Immo.,* vol. 109:842, 1972, "Detection of additional antigenic determinants of hepatitis B antigen".

Charnay et al., *Nuc. Acid Res.,* vol. 7, p. 335, 1979, "Localization on the viral genane and nucleotide sequence of the gene coding for the two major polypeptides of the hepatitis B surface antigen".

*Primary Examiner*—Robin L. Teskin
*Attorney, Agent, or Firm*—Barbara Rae-Venter; Bertram I. Rowland

[57] ABSTRACT

Novel oligopeptides are provided having serologic activity for the a determinant of hepatitis B virus surface antigen. Included in the oligopeptide chain are a sequence of at least two cysteines and a lysine in proximity to the cysteines. The oligopeptides can find use in immunoassays, the formulation of vaccines, and the production of antisera.

4 Claims, No Drawings

SYNTHETIC VACCINE PEPTIDE EPITOMES OF HEPATITIS B SURFACE ANTIGEN

CROSS REFERENCE TO RELATED APPLICATIONS

This is a continuation of application Ser. No. 112,054 filed Jan. 14, 1980, now U.S. Pat. No. 4,415,491.

BACKGROUND OF THE INVENTION

1. Field of the Invention

A basic factor in life is the ability of a vertebrate to distinguish between self and foreign proteinaceous materials. The mammalian immune system relies on the fact that within a short time after birth, defense mechanisms have been elaborated which permit the destruction and neutralization of foreign invading bodies, particularly microorganisms. A prerequisite of this system is its ability to make fine distinctions between differences in primary, secondary, and tertiary structure of proteins.

A significant industry has developed in using the mammalian ability to produce antisera specific for one or more epitopic sites to quantitatively determine a particular compound. In order to produce the antisera, it is necessary to hyperimmunize a mammal with an antigen, so that antibodies are produced which specifically bind to the epitopic sites of the antigen. In many instances, the isolation of the antigen in sufficient amounts can be arduous, in addition to the difficulties involved in purifying the antigen. In some instances, there may be an interest in having antibodies for a specific determinant or epitopic site of an antigen having a plurality of determinant sites.

In the subject invention, there is a further interest in providing an antigenic oligopeptide capable of competing with an antigen determinant site for antisera. In the production of vaccines, where an attenuated virus is injected into a host to induce an immunological response, there are serious problems concerned with the preparation of such vaccines, side effects resulting from the injection of such vaccines, and the potential for the vaccine to induce the disease from which the host was to be protected by the injection. It would therefore be desirable to be able to mimic with a relatively short oligopeptide one or more determinant sites of an infectious virus, where the oligopeptides could serve to initiate the immune response, but otherwise would have no deleterious effects.

One viral disease which has been a major problem in public health and transfusion practice is hepatitis, resulting from hepatitis B virus (HBV) infection. Worldwide research of this problem has led to the development of a variety of vaccines using the hepatitis B surface antigen (HBsAg). Vaccines used in the current clinical trials of vaccines against HBV infections have been most often derived from the plasma of HBV-infected blood donors. The safety and efficacy of such vaccines which use natural viral products must be tested by one-time innoculation of colony bred chimpanzees. Because susceptible chimpanzees are not easily available, and the same chimpanzee cannot be used more than once, the testing of the vaccine can be subject to the availability of a susceptible chimpanzee. In addition, the long term effects of the viral products are not known adequately and alternative approaches to vaccine development warrant serious consideration.

There is therefore ample incentive to develop vaccines which would not require the rigorous monitoring and testing required in the use of the naturally occurring antigens.

2. Brief Description of the Prior Art

The following references give an historical background toward efforts in understanding hepatitis antigen. Vyas and Shulman, Science, 170 332 (1970); Rao and Vyas, Nature New Biology, 241 240 (1973); Rao and Vyas, Microbios (1974) 9, 239; Rao and Vyas, ibid. (1974) 10, 233; Peterson et al. PNAS USA 74 1530 (1977); Vyas et al. ed., Viral Hepatitis Proceedings of UCSF Symposium, Franklin Institute Press, Philadelphia (1978); Valenzuela et al. Nature, 280 815 (1979); Charnay et al., Nucleic Acid Res. 7 355 (1979).

SUMMARY OF THE INVENTION

Novel oligopeptides are provided which may be employed by themselves or extended by additional amino acids as a synthetic analog of an epitopic or determinant site of hepatitis B virus surface antigen, particularly the a determinant. The oligopeptides of this invention find use in the development of immunoassays for hepatitis, as precursors to synthetic vaccines, and in the preparation of antisera recognizing the hepatitis B virus surface antigen.

DESCRIPTION OF THE SPECIFIC EMBODIMENTS

An oligopeptide analog is provided which is mimetic for an epitopic or determinant site of hepatitis B virus surface antigen (HBsAg), particularly the a determinant site, which is common to all types of HBsAg, particularly the four major subtypes adw, ayw, adr and ayr. The oligopeptide has at least six amino acids which six amino acids include a series of cysteines having at least two cysteines and not more than three cysteines in tandem adjacent to a lysine, usually separated by one amino acid from the terminal cysteine of the sequence in the direction going from the N-terminus to the C-terminus. The sequence of three cysteines separated from a lysine by a single amino acid appears to be a unique structure in naturally occurring proteins. Usually, the sequence will involve three cysteines, followed by threonine and then lysine.

For the most part, the oligopeptides of the subject, invention will have the following formula:

$$R-AA^1-AA^2-AA^3-AA^4-(CYS)_n-AA^5-LYS-AA^6-AA^7-AA^8-AA_9-AA^{10}-T$$

wherein:

$AA^{1-10}$ are amino acids or bonds, at least two, usually at least three, of which one is $AA^5$ are amino acids.

R is hydrogen, lysine, arginine, or an oligopeptide of not more than about 50 amino acids.

T is hydroxyl, lysine, arginine, cysteine or an oligopeptide of not more than about 50 amino acids, usually not exceeding 20 amino acids. The total number of amino acids of the compound generally not exceeding 60 amino acids, preferably not exceeding about 50 amino acids.

More particularly, $AA^1$ is a bond or lysine, particularly being a bond when R is lysine;

One of $AA^{2-4}$ is tyrosine or phenylalanine, particularly $AA^2$ or $AA^4$, more particularly $AA^2$, when other than tyrosine or phenylalanine AA$^2$ is a bond or a neutral amino acid;

AA$^3$ is proline or other neutral amino acid;

AA$^4$ is serine or other neutral amino acid;

AA$^5$ is threonine or other neutral amino acid;

AA$^6$ is proline or other neutral amino acid;

AA$^7$ is threonine or other neutral amino acid;

AA$^8$ is aspartic acid or a hydrophilic acidic amino acid;

AA$^9$ is glycine or other neutral amino acid;

AA$^{10}$ is asparagine or other neutral, including neutral polar, amino acid;

R is hydrogen, lysine or an oligopeptide of up to 50 amino acids, more usually up to 30 amino acids, and preferably of not more than about 25 amino acids; and T is hydroxyl, lysine, cysteine or an oligopeptide of up to 50 amino acids, more usually of up to about 20 amino acids, and preferably of not more than about 15 amino acids, more preferably of not more than about 10 amino acids.

By neutral amino acid is intended glycine, aliphatic hydrocarbon C-substituted glycines of from one to nine carbon atoms, particularly alkyl of from one to four carbon atoms, both straight chained and branched, carbocyclic aromatic substituted amino acids, particularly phenyl, p-aminophenyl or p-hydroxyphenyl of from 8 to 10 carbon atoms, oxy substituted aliphatic amino acids of three to six, usually three to five carbon atoms, particularly hydroxy and methoxy substituted alkyl, and thio substituted aliphatic amino acids, particularly thiol or thioether substituted amino acids of from three to six, usually three to five carbon atoms, particularly thiol and methylmercapto substituted alkyl; amide nitrogen alkyl substituted amino with alkyl of from about 1 to 3 carbon atoms; and heterocyclic amino acids, particularly five membered aza heterocycles and indole substituted amino acids. Illustrative amino acids include glycine, alanine, valine, leucine, isoleucine, serine, threonine, methionine, phenylalanine, tyrosine, proline, hydroxyproline and tryptophan, normally of the naturally L-configuration but may have the D-configuration, or N-α-alkyl amino acids, e.g., methyl or ethyl, either L- or D-configurations or P-amino substituted phenylalanine.

The acidic polar amino acids are dibasic amino acids of from four to five carbon atoms. The neutral polar amino acids are the ω-amides of the dibasic amino acids, of from four to five carbon atoms. These amino acids are aspartic acid and asparagine and glutamic acid and glutamine.

The basic amino acids are lysine, arginine and histidine, which may be neutralized by acylation, for example with a carboxylic acid of from one to eight carbon atoms, usually an aliphatic acid of from two to four carbon atoms, or a carbonic acid monoester of from four to ten, usually four to eight carbon atoms.

n is of from one to three, usually three, preferably one when T has cysteine as its N-terminus.

A preferred oligopeptide has the following formula:

R'—AA$^{1'}$—TYR or PHE—PRO—SER—(CYS)$_3$—THR—LYS—PRO—AA$^{7'}$—AA$^{8'}$—AA$^{9'}$—AA$^{10'}$—T' wherein:

AA$^{1'}$ is a bond or lysine;

AA$^{7'}$ is threonine, serine, methionine or an aliphatic amino acid of from two to six, more usually of from two to five carbon atoms;

AA$^{8'}$ is an acidic amino acid being a dibasic aliphatic amino acid of from four to five carbon atoms;

AA$^{9'}$ is a neutral aliphatic amino acid of from two to six carbon atoms, more usually of from two to three carbon atoms;

AA$^{10'}$ is a neutral polar amino acid which is the ω-amide of an aliphatic dibasic amino acid of from four to five carbon atoms;

R' is hydrogen, lysine, or an oligopeptide of up to 30 amino acids, usually not more than 25 amino acids, generally ranging from about one to 24 amino acids; and T' is hydroxyl, lysine, cysteine or an oligopeptide of from one to 20 amino acids, more usually of from about one to 15 amino acids, and preferably from about one, more preferably from about five, to ten amino acids.

A particularly preferred oligopeptide has the following formula:

R''—AA$^{1'''}$—TYR—PRO—SER—(CYS)$_3$—THR—LYS—PRO—THR—ASP—GLY—ASN—T'' wherein:

AA$^{1'''}$ is a bond or lysine;

R'' is hydrogen, lysine, or an oligopeptide of from one to 25 amino acids, preferably one to 15 amino acids, which will be further defined subsequently;

T'' is hydroxyl, lysine, cysteine or an oligopeptide of from one to 15, usually one to ten amino acids, which oligopeptide will be further defined subsequently.

Particularly preferred is where R'' is an oligopeptide to be described subsequently or hydrogen, AA$^{1'''}$ is a bond or lysine when R'' is hydrogen and is preferably a bond when R'' is an oligopeptide; and T'' is hydroxyl or an oligopeptide of from about one to 15, usually one to 10, and preferably about ten amino acids. A further preferred oligopeptide has tyrosine replaced with phenylalanine and/or one or both of the threonines replaced with serine.

For R, R', and R'', the oligopeptide will usually have the following formula:

AA$^{a1}$—AA$^{b1}$—AA$^{a2}$—AA$^{c1}$—AA$^{c2}$—AA$^{c3}$—

AA$^{c4}$—AA$^{c5}$—AA$^{c6}$—AA$^{a3}$—AA$^{bc1}$—AA$^{d1}$—

AA$^{e1}$—AA$^{c7}$—AA$^{d2}$—AA$^{c8}$—AA$^{c9}$—AA$^{b2}$—

AA$^{a4}$—AA$^{f1}$—AA$^{a5}$—AA$^{f2}$—AA$^{c10}$—AA$^{c11}$—

It should be understood, that the oligopeptide may be cleaved at any amino acid to provide a shorter oligopeptide since for many uses a short oligopeptide leader will be desirable. Therefore, it should be understood, that the above formula beginning with the C-terminus can be cleaved between any two amino acids.

The AA$^a$'s are aliphatic amino acids of the following formula:

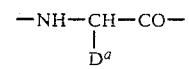

where D$^a$ is hydrogen or an aliphatic group of from one to six, usually one to four carbon atoms, having from zero to one chalcogen atom of atomic number eight to 16 (oxygen or sulfur) is oxy or thio, including hydroxy, thiol and ethers, wherein the ether is an alkyl ether, usually of one carbon atom, i.e. methyl;

$AA^b$ is a neutral amino acid of the formula:

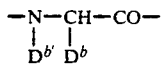

wherein:

$D^b$ has the same limitations as $D^a$, where $D^{b'}$ is hydrogen or $D^b$ and $D^{b'}$ may be taken together to define with the atoms to which they are attached proline or hydroxyproline;

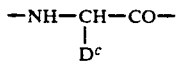

wherein:

$D^c$ is a chalcogen substituted alkyl group of from two to six, usually two to four carbon atoms, wherein the chalcogen may be present as hydroxy, thiol, or methyl ethers thereof;

$AA^{bc1}$ is an amino acid as described for $AA^b$ or $AA^c$, but is preferably the chalcogen substituted amino acid, proline or hydroxyproline;

$AA^d$ is cysteine or may be taken together with another cysteine to define cystine;

$AA^e$ is a basic amino acid of the formula:

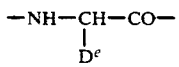

wherein:

$D^e$ is an amino or guanidino substituted alkyl group, normally ω-substituted, with alkyl of from three to four carbon atoms, particularly lysine and arginine;

$AA^f$ is of the formula

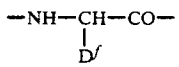

wherein:

$D^f$ is a carboxamide substituted alkyl group of from two to five carbon atoms, particularly two to three carbon atoms, more particularly ω-substituted, for example, asparagine and glutamine.

It should be appreciated, that in going from the C-terminus to the N-terminus, the above oligopeptide may be shortened so that only one or more amino acids may be involved, so that the chain may have one amino acid, not more than five amino acids, not more than ten amino acids, and particularly not more than 20 amino acids. In addition, to modify the properties of the oligopeptide, various amino acids may be changed, so long as there is no significant effect on the spatial and polar characteristics of the determinant site.

For the most part, T, T′ and T″ will have the following formula:

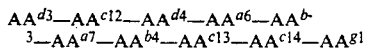

$AA^{d3}$—$AA^{c12}$—$AA^{d4}$—$AA^{a6}$—$AA^{b3}$—$AA^{a7}$—$AA^{b4}$—$AA^{c13}$—$AA^{c14}$—$AA^{g1}$ wherein:

$AA^{a-d}$ have all been defined previously, while $AA^g$ is a heterocyclic substituted amino acid, particularly tryptophan or histidine, more particularly tryptophan. A particularly preferred structure for both the Rs and the Ts are of the following formula respectively:

R = H—ILE—PRO—GLY—SER—THR or SER—THR—THR—SER—THR—GLY—SER or PRO—CYS—ARG or LYS—THR—CYS—THR—THR or MET—THR—PRO—ALA—GLN—GLY—ASN—SER—MET—

T = CYS—THR—CYS—ILE—PRO—ILE—PRO—SER—SER—TRP—OH

Of particular interest in the subject invention are the oligopeptides derived from the HBsAg, a determinant, particularly the 134-146 or 139-147 fragments, or larger fragments incorporating these fragments.

The oligopeptides of this invention are produced in substantially pure form. Thus, usually the subject compositions will be at least 80 mole percent, more usually at least about 90 mole percent of the particular oligopeptide or mixture of oligopeptides which come within a particular formula. The subject compounds are made in conventional ways which can be employed for the production of oligopeptides. Techniques include using automatic peptide synthesizers, employing commercially available protected amino acids. For example, a Beckman Model 990 peptide Synthesizer. Alternatively, recombinant DNA technology may be employed, by synthesizing according to conventional procedures the appropriate nucleotide sequence, joining the sequence to an appropriate replication vector e.g. Adv, pSC101 or pBR322, transforming a microorganism e.g. a bacterium such as E.coli or a yeast such as S.cerevisiae and cloning the transformed bacteria to isolate the oligopeptides of interest.

The subject compounds can be used in a variety of ways as indicated previously. For example, the subject compounds can be used in immunoassays, where the subject oligopeptide is conjugated to a label. Various labels may be included, such as radioactive isotopes e.g. tritium or $^{125}I$, fluorescers, coenzymes, such as heme or NAD, enzymes, or the like. See for example U.S. Pat. Nos. 3,817,837, 3,853,914, 3,850,752 and 3,901,654.

The methods for preparing the various conjugates are well established in the prior art, and do not require exemplification here.

The subject compounds can also be conjugated to an immunogenic carrier, e.g. antigen proteins, to act as a hapten for the production of antibodies specific for HBsAg. Various proteins may be employed as antigens which are not endogenous to the host. Commonly employed antigens are the albumins, globulins, keyhole limpet hemocyanin, or the like. Haptenic conjugates to antigens are well known in the literature and are amply exemplified in a wide variety of patents. See for example U.S. Pat. Nos. 4,156,081, 4,069,105 and 4,043,989.

The subject oligopeptides can also be employed as vaccines, by conjugating the oligopeptides, particularly the shorter oligopeptides, to a protein which results in an immunological response to the oligopeptides. Alternatively, by polymerizing the oligopeptide, a high molecular weight antigen (>5,000 daltons, usually greater than 10,000 daltons), in itself or conjugated to a carrier protein may serve as a vaccine. The ideal protein for conjugation is one which is antigenic in itself, but to which the host is immunized. Of particular interest as a carrier protein is the tetanus toxoid to which the oligopeptide may be joined to provide an antigenic conjugate which will produce an immunological response to the HBsAg. Thus, the host may be immunized against hepatitis without concern as to potential infection.

The synthetic vaccine can be introduced into the host most conveniently by injection, intramuscularly, parenterally, orally or subcutaneously. Any of the common liquid or solid vehicles may be employed, which are acceptable to the host and which do not have any adverse side effects on the host nor any deterimental effects on the synthetic vaccine. Conveniently, phosphate buffered saline, at a physiological pH e.g. pH7 may be employed as the carrier. The concentration of conjugate will generally vary from about 5 to 15, usually 10 μg per injection, while the volume of the solution will generally be from about 0.25 to 1 ml, preferably about 0.5 ml. One or more injections may be required, particularly one or two additional booster injections.

To demonstrate the ability of the subject oligopeptides to compete with the a determinant site of HBsAg, the following oligopeptides were employed in two different test procedures.

P-13 = H—TYR—PRO—SER—CYS—CYS—THR—LYS—PRO—THR—ASP—GLY—ASN—OH

P-9 = MET—GLU—ASN—ILE—THR—SER—GLY—PHE—LEU—OH

Both of these oligopeptides were synthesized in accordance with conventional procedures.

Hemagglutination Inhibition

Human, type 'O' erythrocytes were coated with purified HBsAG by the $CrCl_3$ method (Vyas and Shylman, Science 170:332, 1970; U.S. Pat. No. 3,887,697). The hemagglutination titer of the anti-HBs human antibody (#1 from France) was determined and 4 hemagglutinating (HA) units were utilized in the assay (i.e., a dilution equal to the end point titer divided by 4). At the dilution for 4HA units the antiserum has specificity for the common 'a' determinant because it was neutralizable by all of the 32 HBsAg positive sera of various subtypes previously tested and confirmed as anti-a. Varying concentrations of P-13 were preincubated with the 4 HA units of anti-HBs and this antibody-P-13 mixture was then tested for hemagglutinating activity. As a protein control, equivalent concentrations of BSA were similarly tested in the assay. Serial dilutions of human serum positive for HBsAg and negative for HBsAG served as hemagglutination inhibition controls. The results are summarized in Table I.

TABLE I

| Hemagglutination Inhibition Assay | | | | | | |
|---|---|---|---|---|---|---|
| Inhibiting Antigen | Protein concentration (mg/ml) 20 | 10 | 5 | 2.5 | 1.25 | 0.625 |
| P-13 | + | + | + | + | − | − |
| BSA | − | − | − | − | − | − |
| HBsAG μg/ml | + | + | − | − | − | − |
| | Serum dilution 1:2 | 1:4 | 1:8 | 1:16 | 1:32 | |
| HBsAg + serum | + | + | + | + | + | |
| HBsAg − | − | − | − | − | − | |

TABLE I-continued

| Hemagglutination Inhibition Assay |
|---|
| serum |

+ = Inhibition of hemagglutination
− = Hemagglutination

The peptide (P-13) inhibited the hemagglutination of HBsAg-coated erythrocytes at concentrations of 20, 10, 5 and 2.5 mg/ml. Equivalent concentrations of BSA did not inhibit the hemagglutination.

To exclude the possibility that P-13 inhibited the system nonspecifically, P-13 was tested in an unrelated hemagglutination system. Human, type 'O' erythrocytes were coated with a human, purified, IgA myeloma protein. Four hemagglutinating units of a human anti-IgA antibody were incubated with P-13 at concentrations of 20, 10, 5, 2.5 and 1.25 mg/ml. The IgA present in a normal human serum served as a positive control. The peptide (P-13) demonstrated no inhibition of this hemagglutination assay at any concentration tested.

RIA Inhibition

An RIA for the detection of antibody to HBsAg is commercially available (Abbott). The inhibition of a defined antibody was utilized in this assay as a means of demonstrating the antigenic activity of P-13. The RIA titer of the anti-HBs (#1 from France) antibody was determined and 4 RIA units were utilized in the assay. Equivalent concentrations of P-13, a synthetic peptide of 9 amino acids from the N-terminal sequence of HBsAg (P-9), and BSA were each preincubated with the anti-HBs antibody. They were then tested in the standard RIA for detection of anti-HBs. Purified HBsAg was used as a positive control. The results are summarized in Table II.

TABLE II

| Percent Inhibition of RIA | | | | | | |
|---|---|---|---|---|---|---|
| Antigen | Protein concentration (mg/ml) 20.0 | 10.0 | 5.0 | 2.5 | 1.25 | 0.625 |
| P-13 | 66.9 | 35.9 | 23.4 | 2.3 | 0 | 0 |
| P-9 | — | 0 | 0 | 0 | 0 | 0 |
| BSA | 0 | 0 | 0 | 0 | 0 | 0 |
| | Protein concentration (ng/ml) | | | | | |
| HBsAg | 300.0 | 30.0 | 3.0 | 0.3 | 0.03 | |
| | 95.0 | 86.5 | 19.3 | 10.4 | 0 | |

The P-13 was inhibitory in the RIA at concentrations of 20, 10, 5 and 2.5 mg/ml and the degree of inhibition was dose-dependent. Note that an approximate $10^6$-fold difference (weight/weight) existed between natural HBsAg and the synthetic peptide (P-13) with respect to the degree of inhibition. A large disparity in the antigenicity of natural protein and carbohydrate antigens and their synthetic haptens is not unexpected.

The above data demonstrate that the subject oligopeptides can be employed as mimetic of a hepatitis B virus surface antigen. In two commonly employed tests for the determination of antigenicity, the small oligopeptide effectively competes with the natural antigen. Further enhancement of the effectiveness of the small oligopeptides could be achieved by extension of the oligopeptide from the 13 amino acids to a larger number of amino acids, to further insure maintenance of the desired conformations.

In accordance with the subject invention, small oligopeptides are provided which are mimetic of determinant sites on hepatitis B virus surface antigens, namely the a determinant site. By virtue of their mimetic capability, they find a wide variety of usages and have numerous advantages. First, a specific determinant site is involved, which is common to the various hepatitis B viruses. Secondly, the synthesis is substantially simpler, since the oligopeptide has far fewer amino acids than the natural surface antigen. Furthermore, because of the cross-linking potential for the cysteines, the oligopeptide avoids the complications of the secondary and tertiary structures of the surface antigen.

The subject oligopeptides find use in assays for surface antigens, as vaccines, for the production of antibodies, and the like. For use in a host, the subject oligopeptides avoid the many problems involved with vaccines developed from attenuated viruses, in being incapable of causing disease. Furthermore, the oligopeptides can be readily prepared in pure form, easily conjugated to a wide variety of carriers, and the resulting conjugates used for the purposes described above.

Although the foregoing invention has been described in some detail by way of illustration and example for purposes of clarity of understanding, it will be obvious that certain changes and modifications may be practiced within the scope of the appended claims.

What is claimed is:

1. A composition comprising:

a conjugate in a physiologically acceptable carrier present in an amount sufficient to induce production of antibodies specific for hepatitis B surface antigen (HBsAg) in a host, wherein said conjugate comprises (a) an oligopeptide of the formula R"—AA$^{1"}$—TYR—PRO—SER—(CYS)$_3$—THR—LYS—PRO—THR—ASP—GLY—ASN—T" where:

AA$^{1"}$ is a bond or a lysine; R" is hydrogen, lysine, or a first peptide of the formula H—ILE—PRO—GLY—SER—THY, SER—THR—THR—SER—THR—GLY—SER, LYS—THR—CYS—THR—THR or MET—THR—PRO—ALA—GLN—GLY—ASN—SER—MET, or a fragment thereof;

and T" is hydroxyl, lysine, cysteine, or a second peptide of the formula CYS—THR—CYS—ILE—PRO—ILE—PRO—SER—SER—TRP—OH or a fragment thereof, covalently conjugated to (b) an immunogen to which said host is preimmunized.

2. A composition according to claim 1, wherein said immunogen is tetanus toxoid.

3. A method of producing antibodies in a mammalian host to hepatitis B virus surface antigen (HBsAg), which comprises administering to said host a conjugate in an amount sufficient to activate an immune responds, said conjugate comprising, in a physiologically acceptable carrier, (a) an oligopeptide of the formula

R"—AA$^{1"}$—TYR—PRO—SER—(CYS)$_3$—THR—LYS—PRO—THR—ASP—GLY—ASN—T"

where:

AA$^{1"}$ is a bond of lysine: R" is hydrogen, lysine, or a first peptide of the formula H—ILE—PRO—GLY—SER—THR, SER—THR—THR—SER—THR—GLY—SER, LYS—THR—CYS—THR—THR or MET—THR—PRO—ALA—GLN—GLY—ASN—SER—MET— or fragment thereof;

and T" is hydroxyl, lysine, cysteine, or a second peptide of the formula CYS—THR—CYS—ILE—PRO—ILE—PRO—SER—SER—TRP—OH or a fragment thereof, covalently conjugated to (b) an immunogen to which said host is premunized.

4. A method according to claim 3, wherein said immunogen is tetanus toxoid.

* * * * *